United States Patent [19]

Jeffery et al.

[11] 4,092,846

[45] June 6, 1978

[54] DETECTION OF LIQUID IN A GAS STREAM

[75] Inventors: Thomas C. Jeffery, Lake Charles, La.; Wilmer B. Graybill, Pittsburgh, Pa.

[73] Assignee: PPG Industries, Inc., Pittsburgh, Pa.

[21] Appl. No.: 655,187

[22] Filed: Feb. 4, 1976

Related U.S. Application Data

[63] Continuation of Ser. No. 523,777, Nov. 14, 1974, abandoned, which is a continuation-in-part of Ser. No. 256,081, May 23, 1972, abandoned.

[51] Int. Cl.² .............................................. G01N 33/00
[52] U.S. Cl. .......................................... 73/29; 55/270; 55/218
[58] Field of Search ............... 73/29, 53, 61.1 R, 73, 73/76; 55/270, 218, 465, DIG. 23; 210/65, 151; 340/235, 272; 116/109

[56] References Cited

U.S. PATENT DOCUMENTS

| 790,849 | 5/1905 | Osborne | 55/218 |
|---|---|---|---|
| 1,558,057 | 10/1925 | Sommer | 116/109 |
| 1,769,639 | 7/1930 | Gustafson | 116/109 |
| 1,913,120 | 6/1933 | Kenyon | 73/73 |
| 2,188,511 | 1/1940 | Leighton | 340/27 L |
| 2,268,442 | 12/1941 | Crawford | 340/235 X |
| 2,290,323 | 7/1942 | Graham | 55/446 X |
| 2,954,202 | 9/1960 | Bale | 177/45 |
| 3,067,621 | 12/1962 | Fairhurst | 73/73 |
| 3,155,182 | 11/1964 | Rackman | 177/45 |
| 3,163,729 | 12/1964 | Flagg | 200/61.06 |
| 3,477,208 | 11/1969 | Keller | 55/218 |
| 3,483,673 | 12/1969 | Wellman | 55/218 |
| 3,491,585 | 1/1970 | Hass | 73/29 |

*Primary Examiner*—Anthony V. Ciarlante
*Attorney, Agent, or Firm*—Robert J. Grassi

[57] ABSTRACT

Liquid if present in a gas stream is detected by expanding the volume per unit weight of the gas in a vessel to the point where liquid collects in the bottom of the vessel and weighing the liquid.

9 Claims, 3 Drawing Figures

DETECTION OF LIQUID IN A GAS STREAM

CROSS-REFERENCE TO RELATED APPLICATIONS

This is a continuation of application Ser No. 523,777, filed Nov. 14, 1974 now abandoned which is a continuation-in-part of our application entitled "Detection of Liquid in a Gas Stream", Ser. No. 256,081, filed May 23, 1972 now abandoned.

BACKGROUND OF THE INVENTION

1. Field of the Invention

The invention relates to a method and apparatus for detecting if liquid is present in a gas, and for segregating the liquid from the gas. Specifically, it concerns the method and apparatus for adiabatically expanding the volume of a gas stream and/or reducing the flow of the gas stream until liquid, if present, segregates from the gas stream, and detecting the segregated liquid by collecting and weighing it.

2. Description of the Prior Art

Detection of liquid and its removal from a gas stream is very important, particularly in exothermic chemical reactions such as chlorination, fluorination, etc., where liquid, if present in the gas stream entering the reactor, causes explosions because of the large amount of exothermic heat generated by reaction of the liquid with the reactants. The detection and segregation of liquid in a gas stream is also important in drying and evaporating operations, for if liquid is present in a gas stream used for drying, then the drying operation is prolonged and perfect drying may not occur. Several methods are used to overcome these problems. In one method, extra heat is added to the gas stream to vaporize any liquid present; a method currently employed in chlorination reactions. However, if the heat supply fails, then liquid may be present and disastrous results may follow. In another method, baffles are used to entrain any liquid particles present, as described by C. E. Graham in U.S. Pat. No. 2,290,323, but baffles are not suitable for early detection of the liquid, and furthermore elaborate baffle systems are required when small amounts of liquid occur in a gas stream. In another method, described by Crawford in U.S. Pat No. 2,268,442, gaseous water is chemically absorbed by a solid, such as lithium iodide, to determine the amount present in the gas stream. However, this technique is inapplicable where both gas and liquid particles of the same chemical composition are present, as in vaporized chlorine, for it cannot distinguish between the gas and liquid because the solid absorbs both. These drawbacks are overcome in the present invention which employs a relatively efficient, simple, rapid detection and segregation of the liquid.

SUMMARY OF THE INVENTION

The liquid, if present in the gas stream, is detected by expanding the volume occupied by unit weight of gas stream until the linear speed of the gas stream is reduced in a sufficient amount to the point where, the liquid concentrates in a portion of the gas stream where it is detected by optical measurements, but preferably the speed is reduced to the point where the liquid segregates from the stream and is detected by the simple procedure of collecting it and weighing it. Thus, a gas stream is passed through an apparatus having a vessel constructed and arranged so that the volume of a unit weight of the gas stream within the vessel is increased relative to the volume of gas entering and leaving the vessel in the amount sufficient to reduce the linear speed of the gas stream in the vessel to the point where liquid, if present, segregates from the gas and collects within the sump of the vessel. A means such as a scale or other device continuously or intermittently weighs the vessel to detect the presence of liquid by the weight increase.

DESCRIPTION OF THE PREFERRED EMBODIMENTS

Figure 1:
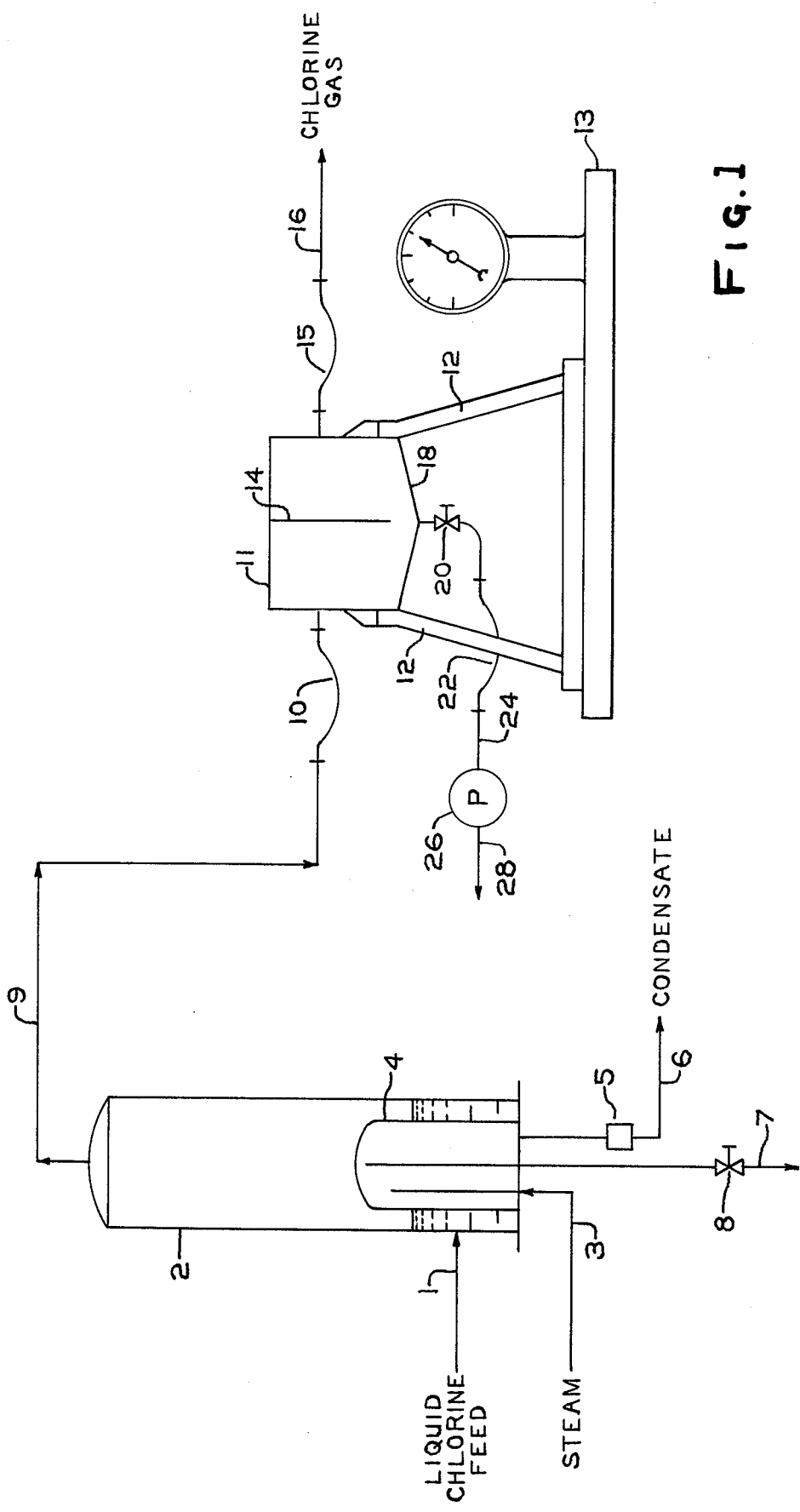
FIG. 1 illustrates a chlorine vaporization unit equipped with the device for detecting the presence of liquid chlorine.

One of the principal forms in which materials are transported and used in the chemicals industry is a stream of gas. It is usually desired that such gas streams be free of liquid, but occasionally, despite precautionary procedures practiced to prevent such an occurrence, the gas stream becomes contaminated with unacceptable amounts of liquid. In order to guard against the introduction of the liquid-contaminated gas stream to a downstream process or storage facility, the presence of liquid must first be detected. The present invention which incorporates by reference the matter of our application, 'DETECTION OF LIQUID IN A GAS STREAM', Ser. No. 256,081, filed May 23, 1972, provides for determining whether liquid is present in a stream of gas by passing the stream of gas through a vessel and weighing the vessel and its contents. Because the vessel represents a constant volume, an increase in weight represents an increase of the average density of the material within the vessel. Moreover, because the differences in densities of liquids and gases are generally quite large, the minor changes in the density of a gas due to ordinary fluctuations in temperature and pressure may be ignored, while the presence of a significant amount of liquid can be detected easily. The vessel may have a sump to trap liquid if present in the stream of gas. In fact, this is the preferred mode of operation. The sump serves to accumulate liquid, thereby increasing the sensitivity of the method. Additionally, it is preferred that the cross-sectional area of the vessel's interior which is normal to the direction of flow be greater than that of the conduit supplying the stream of gas to the vessel. This permits a reduction in linear velocity within the vessel and allows segregation of the liquid and gaseous phases with greater facility.

Weighing may be accomplished intermittently or continuously, but the latter manner is preferred.

This invention is particularly suited for the detection of liquid in a stream of gas where the stream of gas has been produced by the vaporization of a liquid. While the vaporization of the liquid ordinarily proceeds satisfactorily, occasionally unvaporized liquid or condensate will be present in the line normally carrying the gas stream from the vaporizer. Application of the principles of the present invention serves to determine whether such liquid is present in the line.

Of especial importance is the vaporization of liquid chlorine. Large quantities of chlorine are shipped to their destinations in the liquid state in order to reduce shipping costs. The liquid is then vaporized to generate a stream of chlorine gas which is used for its intended purpose, as for example, gas phase chlorinations or oxychlorinations. The unknown introduction of liquid chlorine into such process is usually undesirable since the liquid will provide excessive amounts of chlorine to the system. Detection of liquid chlorine in the line from the vaporizer is, therefore, of considerable importance. By passing the stream of chlorine gas through a vessel and weighing the vessel and its contents, detection of the presence of liquid chlorine, if any, is easily accomplished.

Any of the methods and apparatuses commonly employed to weigh materials may be used to weigh the vessel through which the gas stream is passed. Spring scales, beam scales, balances, flexible beams, strain gauges, and load cells are examples of devices which may be used to detect an increase in weight.

It is often convenient to allow a predetermined increase in weight detected during weighing to initiate an alarm or cause the flow of the stream of gas leaving the vaporizer to be stopped. Several kinds of output can be employed from the weighing device. The closing of a set of contact points can complete an electrical circuit. A valve in a pneumatic system may be opened or closed by the weighing device. The change in resistance of a strain gauge or a load cell may be measured by a change in current or voltage in accordance with known circuits using known principles such as a Wheatstone bridge. Relays, transducers, and amplifiers may be used where appropriate. The alarm is usually a bell, buzzer, gong, siren, light, or similar device. The flow of the gas stream from the vaporizer may be stopped directly, as for example, by a solenoid valve or a pneumatically operated valve position in the line leaving the vaporizer. In this case a pressure relief valve can be used to prevent the build up of excessive pressures in the vaporizer. Preferably, the source of heat to the vaporizer is also cut off. The flow of gas stream from the vaporizer may be stopped indirectly, as for example, by cutting off the supply of heat to the vaporizer. Thus, a valve supplying steam may be closed or a switch supplying electrical energy may be opened. Another manner of indirectly stopping the flow of the gas stream is by shutting off the flow of liquid chlorine entering the vaporizer. Two or more of these methods may be employed together.

The method for detecting the presence of liquid in a gas is illustrated in the vaporization of chlorine by the unit shown in FIG. 1. Liquid chlorine or other liquified gas feeds through line 1 to the vaporizer 2, where steam from line 3 condenses and heats steam dome 4, causing the liquid chlorine surrounding this dome to vaporize and flow through line 9. The steam condensate is collected in stream trap 5 and flows back to the steam generator or to sewer through line 6. During start-up when dome 4 contains air or other gas, valve 8 opens for the air to vent through line 7, and then closes. The vaporized chlorine flows through line 9 and flexible line 10 into vessel 11 and out of the vessel through flexible line 15 and line 16 to the point of its intended use.

Vessel 11 is supported by legs 12 upon weighing scale 13. When chlorine gas enters the vessel through line 10, which has a cross-sectional area smaller than that of vessel 11, it expands, adiabatically, to that point where the linear speed of the gas within the vessel is reduced in a sufficient amount to permit liquid chlorine, if present, to concentrate in the lower portion of the stream where it is detected. Preferably, the decrease in gaseous flow within the vessel is such that the liquid falls from the gas stream and collects within sump 18, causing a weight change which scale 13 detects. The chlorine gas itself flows out through line 15 which has a smaller cross-sectional area than the vessel 11. It is preferred that the collected liquid chlorine, after weighing, feeds back batch-wise through valve 20, flexible line 22, line 24, pump 26, and line 28 to the supply of liquid chlorine or to disposal or other suitable destination. Vessel 11 has a baffle 14 or diverter positioned within the vessel for diverting the gas flow downwardly into the vessel; otherwise, at high flow rates, localized gas flow occurs at the top of the vessel between inlet line 10 and outlet line 15.

Figure 2:
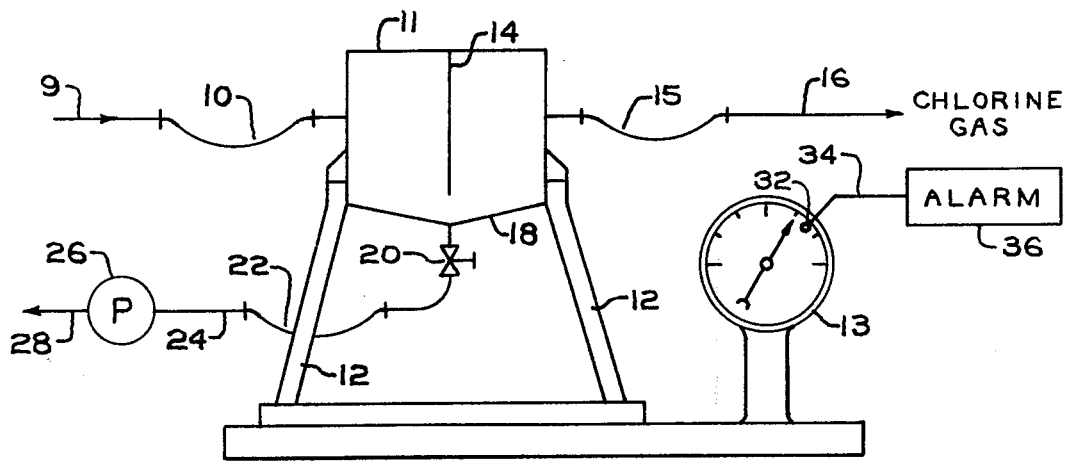
FIG. 2 illustrates a vessel for segregating and collecting the liquid, if present, supported on a scale connected to a warning alarm.
Figure 3:
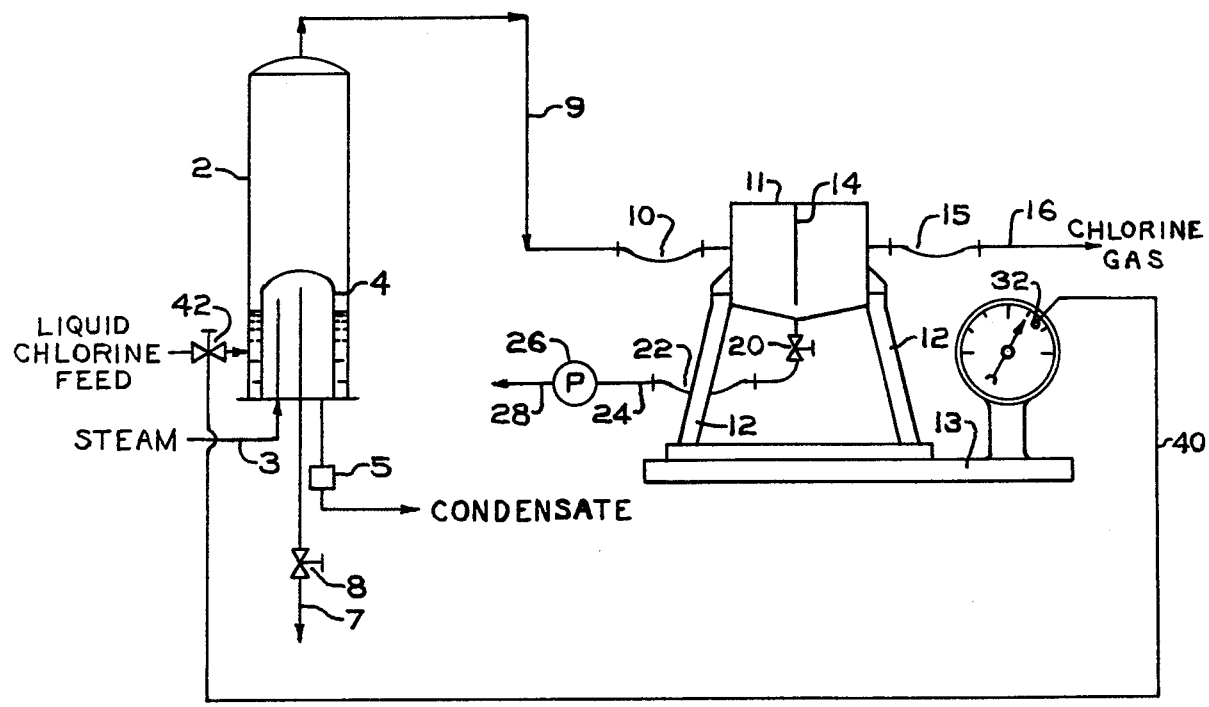
FIG. 3 illustrates a vessel for segregating and collecting the liquid, if present, supported on a scale connected to an automatic valve for stopping the flow of gas when the liquid content reaches a predetermined value.

In other embodiments, weighing scale 13, as shown in FIG. 2, connects through line 34 to an alarm 36, so that when the weight reaches a pre-set point 32, the alarm 36 warns that liquid is present in the gas. Weighing scale 13, as shown in FIG. 3, connects by line 40 to the automatic feed valve 42 so that when the weight reaches a preset point 32 it signals valve 42 to shut off the feed of liquid chlorine.

The specific embodiments of the invention described above, employ the method of increasing the volume of a unit of gas until the flow of gas is such that the liquid segregates out from the gas, collecting the liquid and weighing it. In other embodiments of the invention, the volume of the gas can be increased until the linear speed of the gas stream is reduced to where the pull of gravity upon the liquid particles is sufficiently greater than the collision force of the gas molecules so that the liquid particles concentrate in the lower portion of the gas stream and the increase in concentration is detected by optical measurements, conductivity measurements, etc.

Although chlorine vaporization is specifically shown, other gas vaporization systems are amenable to the invention, such as fluorine, bromine, or steam systems. For example, when steam is wet, that is, liquid droplets of water are present in the steam, these will segregate and be detected by the method and apparatus of this invention. The invention is applicable to systems which vaporize liquid by passing a gas inert to the liquid through the liquid, for if liquid droplets are being carried within the stream of gas, the steps of expanding the stream until the linear speed of the gas is reduced to where the liquid concentrates in the lower portion of the flowing stream and detecting this concentration increase, or where the liquid segregates completely from the stream, collecting the liquid and weighing it are readily accomplished.

While the invention has been described with reference to specific details of certain illustrative embodiments, it is not intended that it shall be limited thereby except in so far as such details appear in the accompanying claims.

We claim:

1. In the method wherein liquid chlorine is vaporized to produce a stream of chlorine gas, the improvement comprising passing said stream of chlorine gas through a vessel wherein liquid and vapor are segregated and weighing said vessel and its contents to determine whether liquid chlorine is present in said stream of chlorine gas.

2. The method of claim 1 wherein said vessel has a sump to trap liquid chlorine if present in said stream of chlorine gas.

3. The method of claim 2 wherein the weighing is performed intermittently.

4. The method of claim 2 wherein the weighing is performed continuously.

5. The method of claim 1 wherein a predetermined increase in weight detected during said weighing initiates an alarm.

6. The method of claim 1 wherein a predetermined increase in weight detected during said weighing causes the flow of said stream of chlorine gas to be stopped.

7. An apparatus for vaporizing a liquid comprising a vaporizer means to which that liquid is fed and means for supplying heat to said vaporizer means, the combination therewith of apparatus for producing a substantially liquid-free vapor stream comprising a vessel, a line feeding fluid to said vessel, a line for removing vapor from said vessel, means within said vessel for segregating liquid from vapor, and means for determining the weight for said vessel.

8. Apparatus as defined in claim 7, characterized in that said apparatus further comprises means responsive to said weighing means for activating an alarm when the weight of said vessel exceeds a predetermined value.

9. Apparatus as defined in claim 7, characterized in that said apparatus further comprises means responsive to said weighing means for decreasing the rate at which liquid is fed to said vaporizer means.

* * * * *